United States Patent [19]

Raysberg et al.

[11] Patent Number: 5,106,583
[45] Date of Patent: Apr. 21, 1992

[54] AUTOMATED PROTEIN HYDROLYSIS SYSTEM

[75] Inventors: Yefim M. Raysberg, Fremont; David R. DuPont, San Francisco; Eric Shulse, Walnut Creek; Jan K. Hughes, San Mateo, all of Calif.

[73] Assignee: Applied Biosystems, Inc., Foster City, Calif.

[21] Appl. No.: 321,230

[22] Filed: Mar. 8, 1989

[51] Int. Cl.⁵ .................................. G01N 35/02
[52] U.S. Cl. ............................ 422/64; 422/63; 422/102; 436/46; 436/86; 73/863
[58] Field of Search .................. 422/63, 64, 80, 81, 422/102, 104; 73/863; 436/46, 86, 175, 178

[56] References Cited

U.S. PATENT DOCUMENTS

| | | | |
|---|---|---|---|
| 3,487,678 | 1/1970 | Thomson et al. | 73/864.85 |
| 3,527,101 | 9/1970 | Sprunger et al. | 73/864.85 |
| 3,536,542 | 10/1970 | Norton et al. | 422/89 |
| 4,221,568 | 9/1980 | Boettger | 422/64 |
| 4,539,296 | 9/1985 | Manabe | 422/64 |
| 4,595,562 | 6/1986 | Liston et al. | 422/64 |
| 4,855,108 | 8/1989 | Masuda et al. | 422/58 |

Primary Examiner—W. Gary Jones
Assistant Examiner—Todd J. Burns
Attorney, Agent, or Firm—Donald R. Boys; Joseph H. Smith

[57] ABSTRACT

Protein analysis apparatus has porous sample supports enclosed in holes in a sample slide. Slides are delivered to hydrolysis and derivatizer stations by a rotating turret such that moveable heads at the stations form closed reaction chambers with the slides, sealing around the holes in the slides and enclosing the sample supports. Tubings connected to the heads deliver substances for reaction, derivatization and cleaning. Protein samples applied to sample supports at one position on the turret are delivered sequentially to hydrolysis and derivatizer stations, and operations are computer controlled. Derivatives are automatically delivered for chromatographic analysis, and supports are automatically cleaned with solvents and purge gas after derivatization and before return to a sample load position. Closed reaction chambers formed by the moveable heads can be heated and pressurized as required for processing.

9 Claims, 11 Drawing Sheets

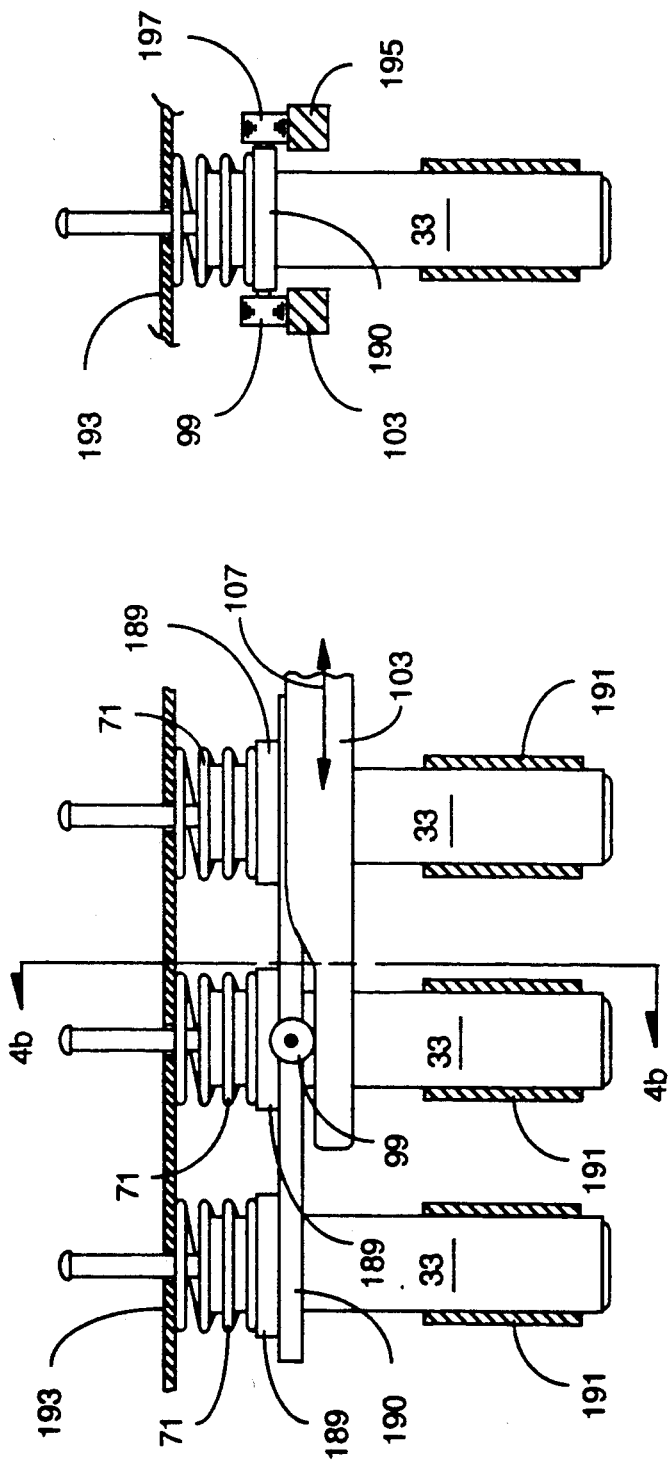

PROTEIN COMPOSITIONS

| AA | Hemoglobin | B-Gal | Pepsin | Pyr. Kinase | Alc Dehyd | Transferrin |
|---|---|---|---|---|---|---|
| Asp | 26.5 (25) | 90.9 (111) | 42.5 (42) | 48.9 (50) | 24.2 (27) | 74.5 (79) |
| Glu | 12.6 (16) | 106.9 (120) | 17.6 (26) | 31.8 (52) | 25.9 (29) | 41.4 (59) |
| Ser | 14.1 (16) | 59.2 (60) | 35.5 (44) | 24.2 (25) | 19.1 (21) | 36.9 (41) |
| Gly | 17.9 (20) | 88.5 (71) | 28.7 (35) | 36.6 (42) | 41.9 (44) | 53.9 (50) |
| His | 18.5 (19) | 34.2 (34) | 1.9 (1) | 15.9 (18) | 10.3 (10) | 21.1 (19) |
| Arg | 7.6 (6) | 54.6 (66) | 3.9 (2) | 35.4 (32) | 10.4 (8) | 29.7 (26) |
| Thr | 20.7 (16) | 55.7 (56) | 34.9 (26) | 36.2 (25) | 16.9 (15) | 39.8 (30) |
| Ala | 36.0 (36) | 77.0 (77) | 17.0 (17) | 58.0 (58) | 35.0 (35) | 57.0 (57) |
| Pro | 14.1 (14) | 74.3 (62) | 16.7 (15) | 20.5 (20) | 16.9 (13) | 33.2 (32) |
| Tyr | 6.2 (6) | 26.4 (31) | 18.1 (16) | 10.3 (8) | 11.6 (14) | 27.8 (26) |
| Val | 29.9 (31) | 60.9 (64) | 22.9 (22) | 49.7 (44) | 25.0 (36) | 46.4 (45) |
| Met | 1.3 (3) | 17.2 (23) | 1.5 (4) | 14.2 (22) | 6.4 (6) | - (9) |
| Cys | - (3) | - (16) | 2.1 (6) | - (8) | 3.1 (8) | - (38) |
| Ile | - (0) | 40.1 (39) | 26.1 (25) | 37.7 (37) | 15.4 (20) | 19.2 (15) |
| Leu | 40.9 (36) | 92.9 (96) | 30.5 (27) | 47.1 (36) | 23.2 (24) | 67.1 (59) |
| Phe | 16.9 (15) | 38.2 (38) | 16.1 (14) | 19.3 (17) | 8.4 (8) | 31.2 (28) |
| Trp | - (2) | - (39) | - (5) | - (8) | - (5) | - (8) |
| Lys | 21.9 (22) | 24.2 (20) | 2.9 (1) | 42.3 (36) | 22.8 (24) | 61.1 (58) |
| # Res | 287 | 1023 | 328 | 529 | 347 | 679 |
| MW | 30,983 | 116,351 | 33,000 | 57,900 | 36,706 | 75,181 |
| Amount hydrolyzed | 0.2 ug | 0.1 ug | 0.2 ug | 0.2 ug | 0.3 ug | 0.04 ug |

Fig. 6

AUTOMATED PROTEIN HYDROLYSIS SYSTEM

FIELD OF THE INVENTION

The present invention is in the area of apparatus for analyzing unknown isolated proteins by breaking the bonds between amino acids by hydrolysis. The invention relates more specifically to automated equipment in which samples may be processed by preprogrammed information.

BACKGROUND OF THE INVENTION

Analysis of unknown proteins is a very important technical ability in biochemistry, and has many applications in the fast growing biochemical related industries. There are a number of different techniques that have been developed and apparatus designed to facilitate the procedures. As an example, preparative gel electrophoresis apparatus has been developed and automated for separating macromolecules, such as proteins, in a sample mixture of unknown materials.

After isolating a protein, it is often desirable to break the strong peptide bonds by which the constituent amino acids are chained, and to tag and quantify the individual amino acids to help identify the protein. It is in this latter general procedure that the present invention has most utility.

One method by which peptide bonds may be broken is through hydrolysis by the action of a strong mineral acid, such as hydrochloric acid (HC1). In a manual laboratory technique, a number of isolated protein samples may be placed in individual containers, such as test tubes, and the tubes then placed upright in a larger container, such as a beaker, which will completely enclose the separate tubes. The upright tubes containing proteins are left open to the inside of the beaker. A concentrated solution of an acid, typically HC1, is placed in the bottom of the beaker, not in direct contact with any of the proteins. The top of the beaker is closed by a suitable method, and heat is applied, causing the HC1 solution to form a vapor in the closed beaker. The vapor contacts the protein sample in each test tube, and over a period of time, the peptide bonds are broken, reducing each protein sample to its constituent amino acids. After the hydrolysis, each of the samples may be introduced by suitable techniques for chromatographic analysis.

The hydrolysis process requires the addition of heat, and intimate contact between the protein and the vapor. The process is also rather slow, and a sample may require typically 20 hours or more at process conditions for the complete dissolution of the bonds in a protein sample. One of the reasons the process takes a lot of time is the limited area of contact between the HC1 and the protein sample. If the dissolution is not complete, the analysis may be faulty.

Another difficulty in this kind of analysis, as in others, is a requirement for clean apparatus and technique so that one sample is not contaminated by another, causing error in the analysis. In the manual procedure, processing more than one sample at a time accepts a risk of cross contamination between samples. Also, there is often a loss of sample in the removal from the beaker after hydrolysis. Moreover, the apparatus must be thoroughly and manually cleaned between procedures.

After hydrolysis is performed, it is still necessary that each sample be tagged, which is a process of exposing the sample to a tagging solution such as phenylisothiocyanate, often with mild heating. Then the samples are introduced for chromatographic analysis, where UV absorption techniques produce measurements, which, by comparison with results from standard samples, may be used to determine the amino acid composition of a protein.

The overall sequence of processes from protein preparation to identifying chromatogram is time consuming, subject to considerable human and equipment error, and open to contamination at several stages. Control is uncertain. What is clearly needed is an automated apparatus in which hydrolysis and derivatization of protein samples may be quickly and efficiently accomplished under programmed control. Such apparatus needs to maximize reaction velocity, provide for simple and efficient automatic cleaning, perform all needed steps without manual intervention, and provide for operation with a large number of samples.

SUMMARY OF THE INVENTION

In accordance with a preferred embodiment of the invention, apparatus is provided for hydrolyzing purified protein samples with a high degree of automation. A portion of the apparatus is made up of a unique reaction chamber system which uses a sample support system having two sides, one side for supporting a protein sample, while permitting fluids to pass therethrough. A holding element holds the sample support system. The apparatus has a first head that has a seal for sealing the first head to the holding element, for enclosing the protein sample in a first volume between the sample support system and the first head, the first head having a fluid passageway connected thereto. The apparatus also includes a second head for providing a second volume on the other side of the support system, the second head having a heating element for gasifying liquid materials in said second head. The second head also has a seal for sealing the second head to the holding element, so that the first and second volumes make up a combined volume that contains the sample support system and the protein sample. The apparatus also includes a driver for moving the first and second heads toward the holding element for sealing the first and second heads thereto, and for moving the first and second heads away from the holding element for opening the first and second volumes and exposing the sample support system. In the preferred mode, the heating element includes a heated spiral passageway connected to the second volume.

In the context of the instrument, the reaction chamber makes up only a small part of the apparatus. The instrument in the preferred embodiment has a rotatable turret that carries sample slides (the holding element above) to hydrolysis stations located around the periphery of the turret for processing. The sample slides have holes containing unique porous sample supports (the support system above) such that protein samples applied to the porous supports adhere to the material of the supports without occluding the flow of other fluids through the supports. The sample supports expose a maximum surface area of protein sample to processing fluids, maximizing reaction rate to provide an exceptionally short processing time.

At the hydrolysis stations, the moveable heads with seals are arranged to contact opposite sides of a sample slide forming the closed reaction chamber. As indicated earlier, the reaction chamber encloses the sample support within a sample slide, thereby completely enclosing a protein sample delivered to the station for processing. The passageways in the heads are connected by fluid tubings to a system of solenoid operated valves and reservoirs for delivering inert purge gas and chemicals for reaction. Heads in the preferred embodiments also have heaters and temperature monitors for controlling temperature of the reaction chamber during processing, and closure of valves on both sides of a reaction chamber allows pressure to be raised above ambient pressure.

An alternative preferred embodiment also includes a derivatizer station for dissolving the amino acid derivatives of the hydrolysis process and delivering the derivatives in solution for chromatographic analysis. The derivatizer station has moveable heads similar to the heads at the hydrolysis station. At the derivatizer station, after the derivatives are removed from the sample supports, the supports may be thoroughly cleaned with solvents from connected reservoirs and dried with inert gas, so clean supports are automatically presented to an operator for loading new protein samples for analysis.

In the preferred embodiments operations are computer controlled through an operator interface comprising menu selection maximizing throughput of samples, flexibility and efficiency.

BRIEF DESCRIPTION OF THE DRAWINGS

FIG. 1b is an elevation view of an hydrolysis station from a vantage point of FIG. 1a.

FIG. 1d is an elevation view of a derivatizer station from a vantage point of FIG. 1a.

FIG. 4a shows an arrangement of elements for advancing and retracting the heads at a hydrolysis station according to a preferred embodiment.

FIG. 4b is a section of FIG. 4a taken along line 4b—4b.

FIG. 6 is a table of results of actual runs with the Hydrolyzer/Derivatizer of the preferred embodiment.

DESCRIPTION OF THE PREFERRED EMBODIMENTS

Figure 1A:
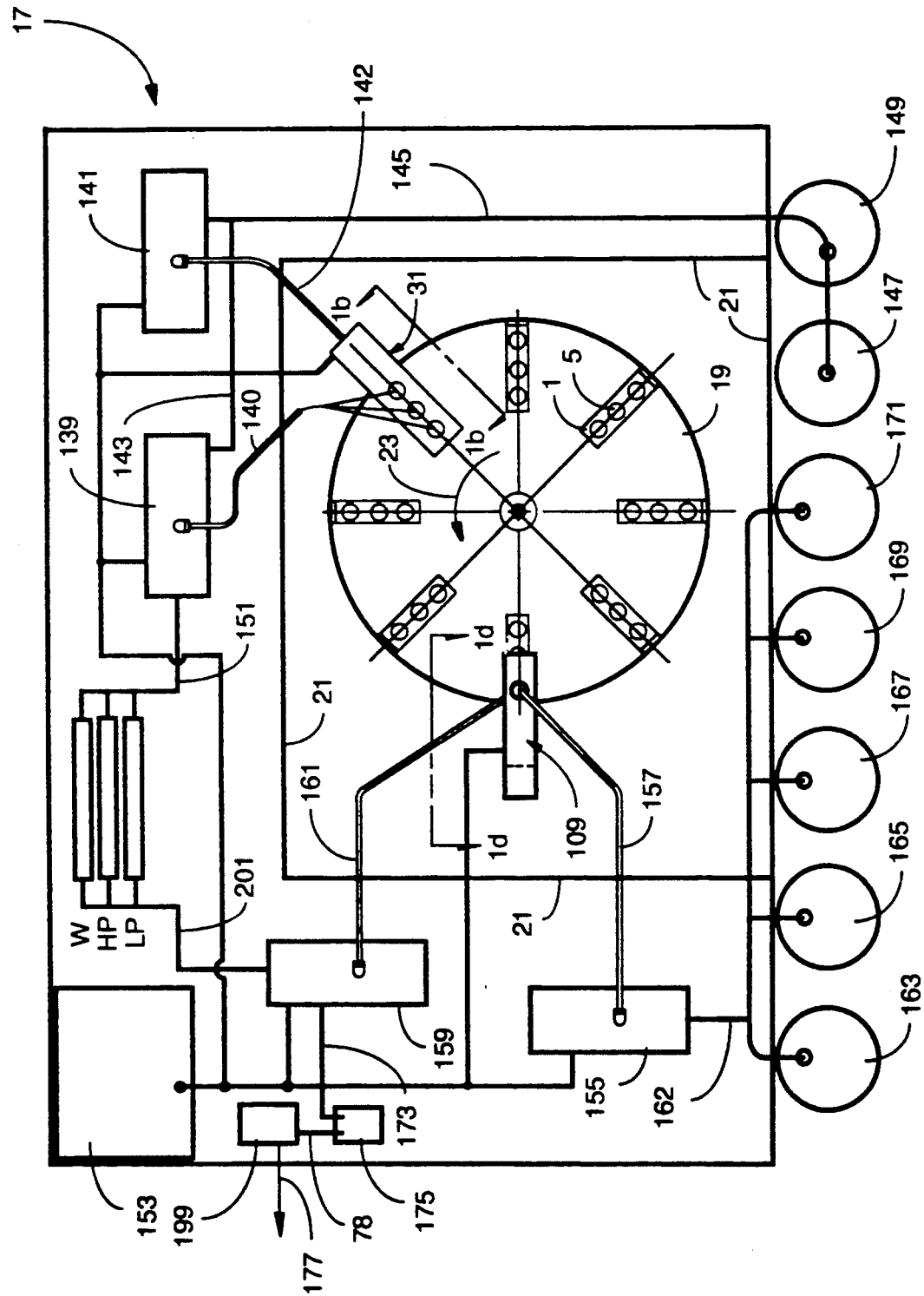
FIG. 1a is a block diagram of a preferred embodiment of the invention showing the general arrangement of principal elements.

FIG. 1a is a plan view block diagram of an instrument 17 according to a preferred embodiment of the present invention. Instrument 17 performs automated hydrolysis of isolated protein samples, tags the derivatives, and transfers the derivatives for appropriate chromatography. Isolated protein samples are placed on sample supports 5 in sample slides 1 that are carried on a rotatable turret 19. The sample slides are glass, and the sample supports are porous glass frit in holes of the glass slides. In the preferred embodiment, there are three holes through each slide, each containing a frit sample support 5.

The rotating turret is inside a dust free enclosure of the instrument formed by walls 21. The turret has nest positions for the slides, such that the lower side of a slide is accessible from beneath the turret, and the upper side is accessible from above the turret. The turret is accessible through a door, not shown, through one wall of the instrument, so that slides may be placed on the turret or removed. In the preferred embodiment the turret is also easily removable, so the entire turret may be replaced, if desired, to facilitate procedures such as sample preparation and service. Also, samples may be loaded on to sample supports in the slides through the access door.

Turret 19 is moved by conventional mechanism, not shown, below the turret. In the preferred embodiment there are twenty-four nests for slides on the turret, and the turret rotating mechanism moves 15 degrees for each position. In practice there may be more nest positions or fewer, and the rotating mechanism is chosen to suit. The turret or delivery vehicle may be changed as well, since a rotating turret is but one of many useful transport devices by which slides might be moved. Turret movement may be in either rotary direction, but is typically in the direction of arrow 23. In the interest of clarity, just eight positions are shown on the turret in FIG. 1a. Samples are typically placed on sample supports and carried to processing stations by movement of the rotating turret. The diameter of turret 19 in the preferred embodiment is about 33 cm.

Figure 1B:
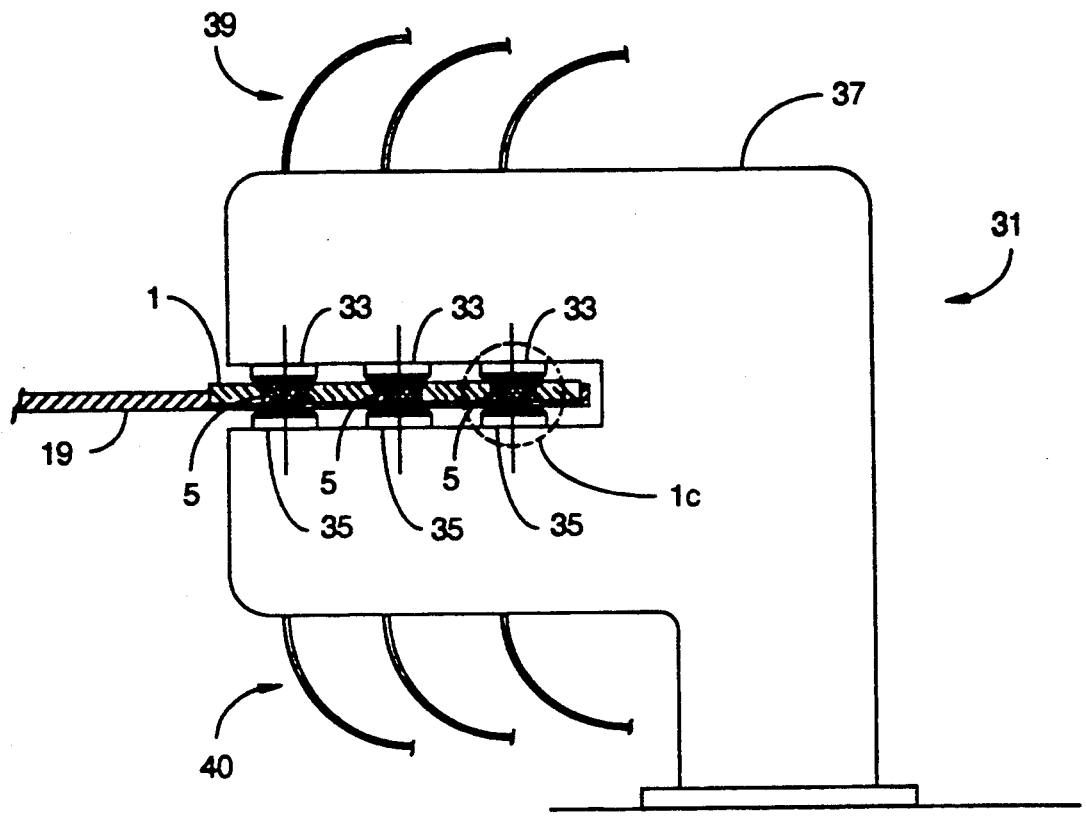

Station 31 is the hydrolysis station in the preferred embodiment. FIG. 1b is an elavation view from the vantage of line 1b—1b of FIG. 1a in the direction of the arrows. In the view of FIG. 1b the turret is sectioned along the centerline of the slide position to show a slide 1, also sectioned, with sample supports 5, relative to other elements at the hydrolysis station. Hydrolysis station 31 has three upper reaction chamber heads 33 and three lower reaction chamber heads 35, all mounted retractably in a body 37 such that the upper heads may be advanced to contact a slide in the hydrolysis station and the lower heads may be simultaneously raised to contact the underside of the same slide. In the retracted position, which is the position shown in FIG. 1b, the turret may be rotated to move a slide, after processing, away from the hydrolysis station, and to bring a new slide for processing to the hydrolysis station. Lines 39 and 40 are electrical and fluid lines leading from each of the upper and lower heads to other elements away from the hydrolysis station.

Figure 1C:
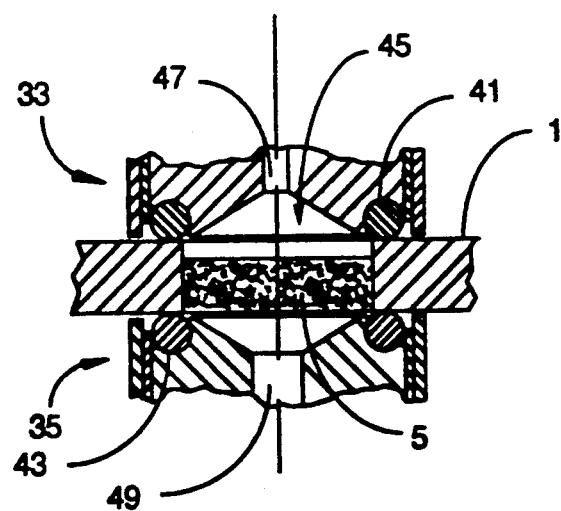
FIG. 1c is a close-up, in section, of a sample support enclosed by heads at the hydrolysis station of FIG. 1b, forming a reaction chamber.

FIG. 1c is an enlarged view of the area of FIG. 1b shown by broken circle 1c, except that the upper and lower heads in view 1c are advanced rather than retracted, and the heads are in contact with sample slide 1.

In system operation in the preferred embodiment all of the heads advance at the same time after a slide arrives at the hydrolysis station on the rotating dial. Also in FIG. 1c the portions of both the upper and lower heads that are included in the figure have been sectioned so that elements internal to the heads may be seen.

Upper head 33 is in contact with the sample slide around the circumference of a seal ring 41 and lower head 35 is in contact with the underside of the slide around the circumference of a seal ring 43. The seal ring material in the preferred embodiment is a material called Kel-Raz, which can withstand the corrosive nature of some of the materials used in processing, such as hydrochloric acid. The movement of the two heads to contact the slide forms an enclosed reaction chamber 45, and the sample support within the opening in the slide is enclosed in this reaction chamber. The upper head has a passage 47 providing an opening into the reaction chamber, and the lower head has a passage 49 providing another opening into the reaction chamber. The openings lead through other portions of the heads (not shown in FIG. 1c) and connect to flexible tubings by which substances may be introduced to and withdrawn from the reaction chamber formed by the two heads and the sample slide. The tubings are included in lines 39 and 40 of FIG. 1b. A similar reaction chamber is formed at the other two sample positions on the slide.

The formation of reaction chambers enclosing sample supports by the action of moveable heads with seals against sample slides moved into position relative to the heads by the rotating turret provides a unique and advantageous apparatus for performing chemical procedures automatically. The upper and lower head portions of the reaction chamber remain at the station after opening, and the sample support portion moves on with the slide as the dial indexes. A significant advantage is that all of the portions of the reaction chamber are easily accessible for service procedures, such as inspection. Cross-contamination is less of a problem, and analytical procedures can be performed with a high degree of accuracy and consistency.

Hydrolysis of polypeptides by acid reaction is a phenomenon well known in the art and is described in many textbooks and reference works. A typical procedure utilizes 6N hydrochloric acid (HCl) and is performed in an oxygen-free environment at elevated temperature (110° C. is typical) and requires typically twenty hours or more to accomplish, depending on protein accessibility to HCl. The apparatus of the preferred embodiment allows the procedure to be automated, and significantly speeds the operation as well. One of the features of the invention that facilitates the performance of the hydrolysis reaction is the sample slide with the associated sample supports.

SAMPLE SLIDE AND SUPPORTS

In the preferred embodiment protein samples are placed individually upon sample supports of an especially designed glass frit. The sample supports hold a protein sample while providing exposure of a maximum amount of surface of the sample for reaction with other introduced substances. Such introduced substances may be caused to pass through the porous frit, contacting the protein sample in transit, and the flow velocity and mass flow rate may be controlled such that the sample is substantially undisturbed on the frit support. This is possible because the design of the sample support is such that the sample material, by virtue of its surface tension, forms to the elements of the porous frit sample support without significantly occluding the openings through the frit. Introduced substances may be gases, vapor phase, or liquid, such as a buffer solution.

Figure 2A:
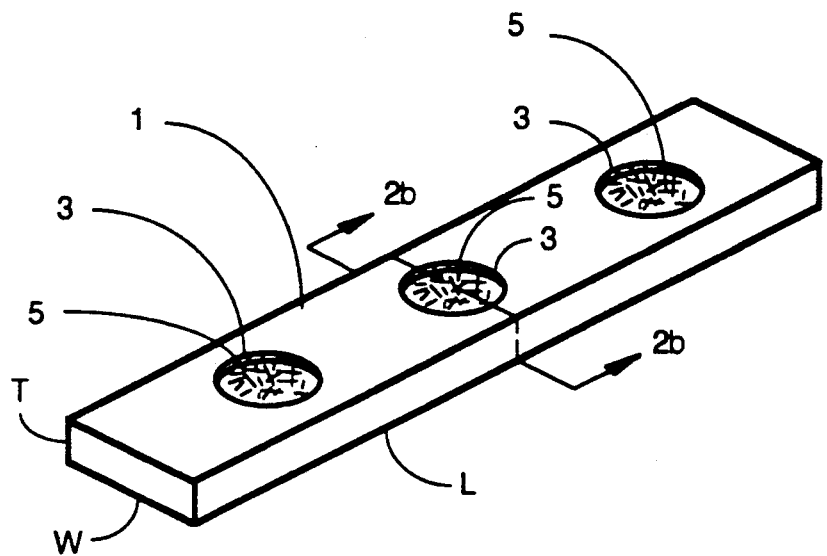
FIG. 2a is an oblique view of a sample slide according to a preferred embodiment.

FIG. 2a shows a sample slide 1 with three holes 3 containing the above-mentioned glass frit sample supports 5. Slide 1 is borosilicate glass in the preferred embodiment, and holes 3 for the sample supports are holes through the glass slide. Other materials that could withstand the temperature used in the process, typically about 165 degrees C., and not contaminate the samples as a result, could be used. It is important that the material have a high degree of resistance to acids and solvents. Quartz is an example of such a material. Glass is preferred because of lower cost and ease of fabrication. In the preferred embodiment length L of the slide is about 8.2 cm., width W is about 2 cm., and thickness T is about 0.5 cm. The diameter of each hole 3 in the preferred embodiment is about 1 cm. Those skilled in the art will realize that these dimensions are merely exemplary, and that these sizes can vary substantially.

Figure 2B:
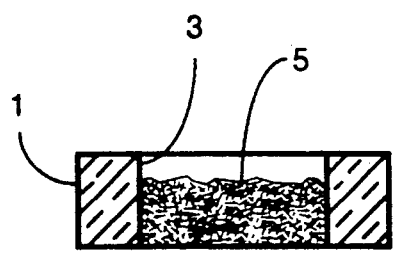
FIG. 2b is a section of FIG. 2a taken along the line 2b—2b, showing a sample support in the sample slide.

FIG. 2b is a section view taken through the slide of FIG. 2a and one of the sample supports along section line 2b—2b. Frit sample support 5 comprises a large number of borosilicate glass rods fused into an open, porous mass. In the preparation of the sample support, slide 1 with holes 3 is placed on a flat surface, such as a surface of graphite, which will withstand glass fusion temperatures but will not adhere to the glass. In the preferred method, drawn and fire-polished glass filaments of about 0.25 mm. diameter are bundled and cut into lengths of about 1 to 3 mm. The resulting short glass rods are poured into each of the holes 3, then the temperature is raised until the rods fuse to one another at the points that they contact, and also fuse to the walls of the hole in the slide at the contact points. Care is taken to avoid excessive heating, beyond which the rods will slump and reduce the porosity of the resulting sample support.

Figure 2C:
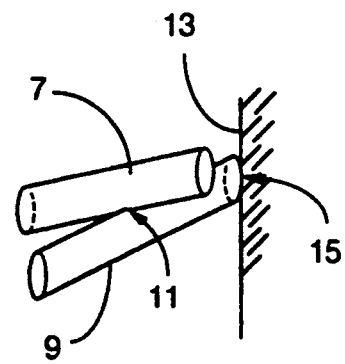
FIG. 2c is a magnified view of two constituent rods of the sample support of FIG. 2b.

FIG. 2c is a greatly amplified view of a small portion of a sample support showing one glass rod 7 lying across another glass rod 9 near a wall 13 of a hole is a slide. The rods are fused and adhere at point 11. Rod 9 touches wall 13 and adheres at point 15. A liquid protein sample is applied to the sample support in a quantity such that the rods are wetted and the sample is held in position in the support due to the surface tension of the liquid sample relative to the glass rods. The sample does not completely fill the spaces between rods, so a gas, vapor, or even another liquid may pass through the sample support with the protein sample present. In so doing a large surface area of the sample is presented to a substance that passes through the support. The surface area presented is substantially equal to the combined surface area of all of the rods that comprise the sample support.

In the development of the sample support, supports were fabricated from small glass particles prepared in a number of different ways, such as crushed and powdered glass. It was found that irregular particles such as crushed and powdered glass formed structures with surface areas that were rough and irregular, such that sample material was difficult to wash away completely during cleaning operations, and there was unacceptable contamination of subsequent analytical procedures. The structure formed by the glass rods has a total surface area formed largely of smooth, fire-polished surfaces, these being the cylindrical surfaces of the rods. The cut ends of the rods still tend to be rough, but the cut ends are a very small portion of the total surface area. Contamination from sample to sample is reduced dramatically.

HYDROLYSIS HEADS AND OPERATION

Figure 3A:
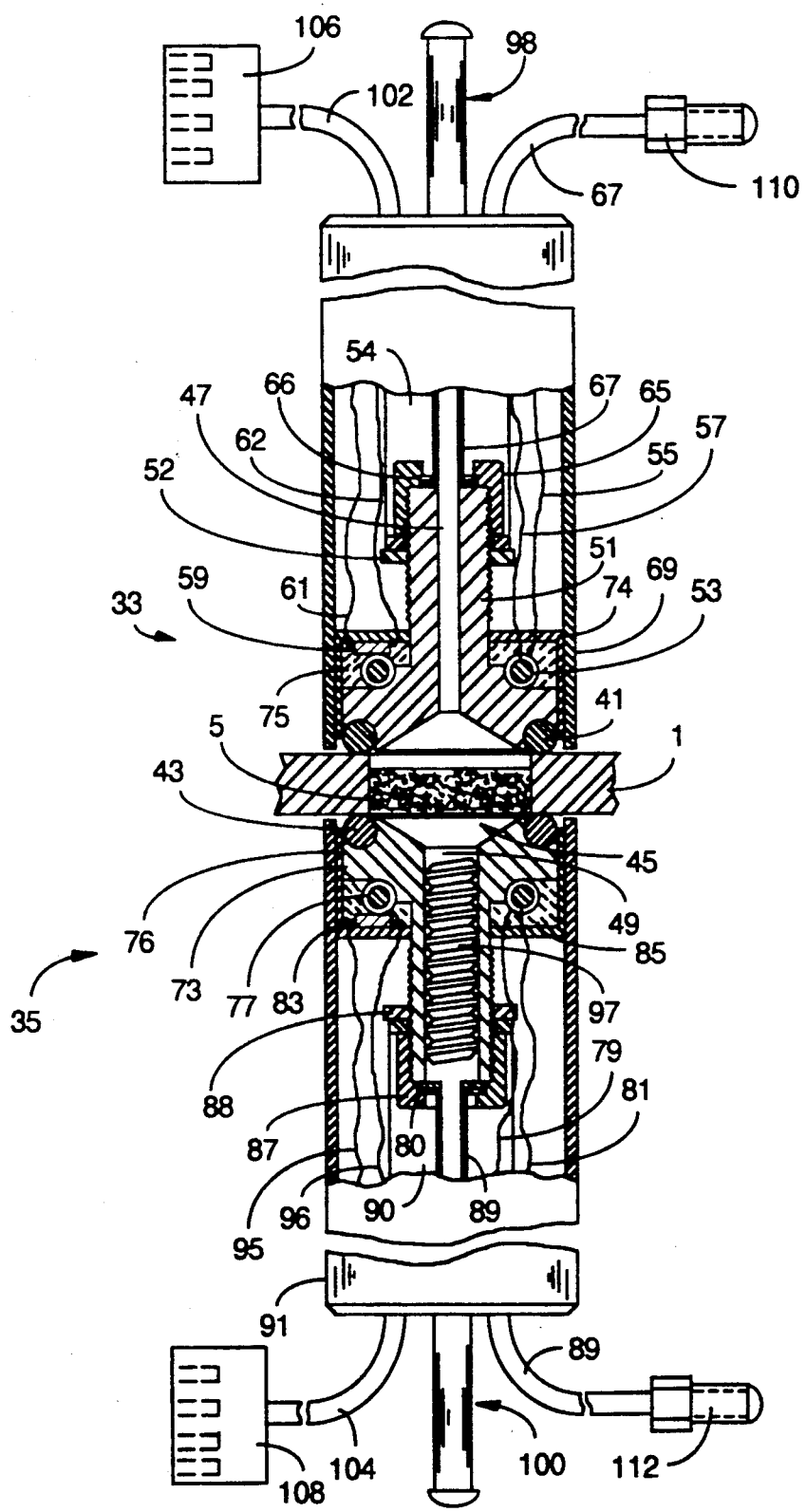
FIG. 3a is an elevation view of an upper and lower head at an hydrolysis station, mostly in section, forming a reaction chamber with a sample support in a sample slide.

FIG. 3a shows reaction chamber 45 formed by the upper and lower heads advanced to contact the upper and lower surfaces of a sample slide, similar to FIG. 1c, except that the section is continued through most of the upper head 33 and a lowerr head 35.

Upper head 33 comprises a metal body 51 with a radiused step for seal ring 41. The material of the metal body in the preferred embodiment is Tantalum, which is not degraded by the strong acid used in the processing. A resistance heating element 53 fits in a second radiused groove on the body and electrical power leads 55 and 57 supply power to the heating element. In the preferred embodiment the heating element is silver-soldered to the Tantalum body to provide for efficient heat transfer to the body. A thermistor 59 senses temperature and has control leads 61 and 62.

A teflon enclosure 74 forms a closed space with body 51, such that both the thermistor and the heating element are in the closed space. The thermistor and the heater are encapsulated in a heat conducting material 75, injected into the enclosed space between enclosure 74 and body 51, such as an epoxy containing a metal powder to enhance heat conductivity. After encapsulation, the teflon enclosure, body 51, the thermistor, and the heater are an integrated unit. The teflon enclosure has holes for the heater and thermistor leads, and for injection of the encapsulating material.

Body 51 is threaded externally and a retainer nut 65 positions and holds the flanged end of a teflon tubing 67 with the aid of a washer 66. The tubing is for delivering substances to the reaction chamber at appropriate times for processing steps and for withdrawing substances as needed. A pusher assembly 98 comprises a bracket 54 which is fastened to body 51 by means of a lock nut 52. The purpose of the pusher assembly is to push the inner elements of a head out of enclosure 69 to provide easy access to the seal ring for service. Teflon tube 67 exits at the end of the head away from the seal ring, and has, in the preferred embodiment, a connection fitting 110 for connection to lines to other plumbing of the instrument. The electrical lines for the heater and the thermistor exit the head in a bundle 102 and terminate at a four prong plug 106. The electrical and fluid lines each extend a distance of about 20 cm. from the head in the preferred embodiment, and the connectors provide service modularity.

A lower head 35 has a Tantalum body 73, a resistance heater 77 with power leads 79 and 81, a thermistor 83 with control leads 95 and 96 encapsulated in material 85 within a teflon enclosure 76, and a retainer nut 87 holding the flanged end of a tubing 89 with the aid of a washer 80. An outer stainless steel enclosure 91 encloses the internal elements. Seal ring 43 in the lower head bears against the underside of a slide to form the seal for the lower portion of the reaction chamber. A pusher assembly 100 comprises a bracket 90 fastened to body 73 with a lock nut 88. Teflon tubing 89 extends from the head in an umbilical of about 20 cm. length, ending in a connector 112. Electrical leads 79, 81, 95 and 96 form a single umbilical 104 of about 20 cm. length in the preferred embodiment, and terminate at a four prong connector plug 108.

The lower head differs from the upper in the flow passage through the Tantalum body. Upper passage 47 is about 0.8 mm. in the preferred embodiment. The outer thread of body 51 is #10-32, and the overall length of the body is about 3 cm. Passage 49 through the lower head is about 2.6 mm, but is not an unobstructed passage through body 73. A threaded stud 97 is threaded $\pi$4-40 in the preferred embodiment, and has the outer diameter of the threads machined to be a press fit with the bore of passage 49. Stud 97 is about 2.5 cm. in length, and is pressed completely into passage 49. The purpose of the threaded stud is to increase the overall effective length of the passage and to create a stored volume of material. Material introduced to the reaction chamber from below through passage 49 must pass around the spiral of the threads of the threaded stud. The development of the long passage has the advantage of bringing material into the heating zone comprising the heating element and the Tantalum body, and keeping the material in the heating zone longer during passage into the reaction chamber. A further advantage is that a large surface area is provided between the heating body and the substance to be heated. Another advantage is that a relatively large volume of material may be supplied in a procedure that requires that the reaction system be closed during processing.

Figure 3B:
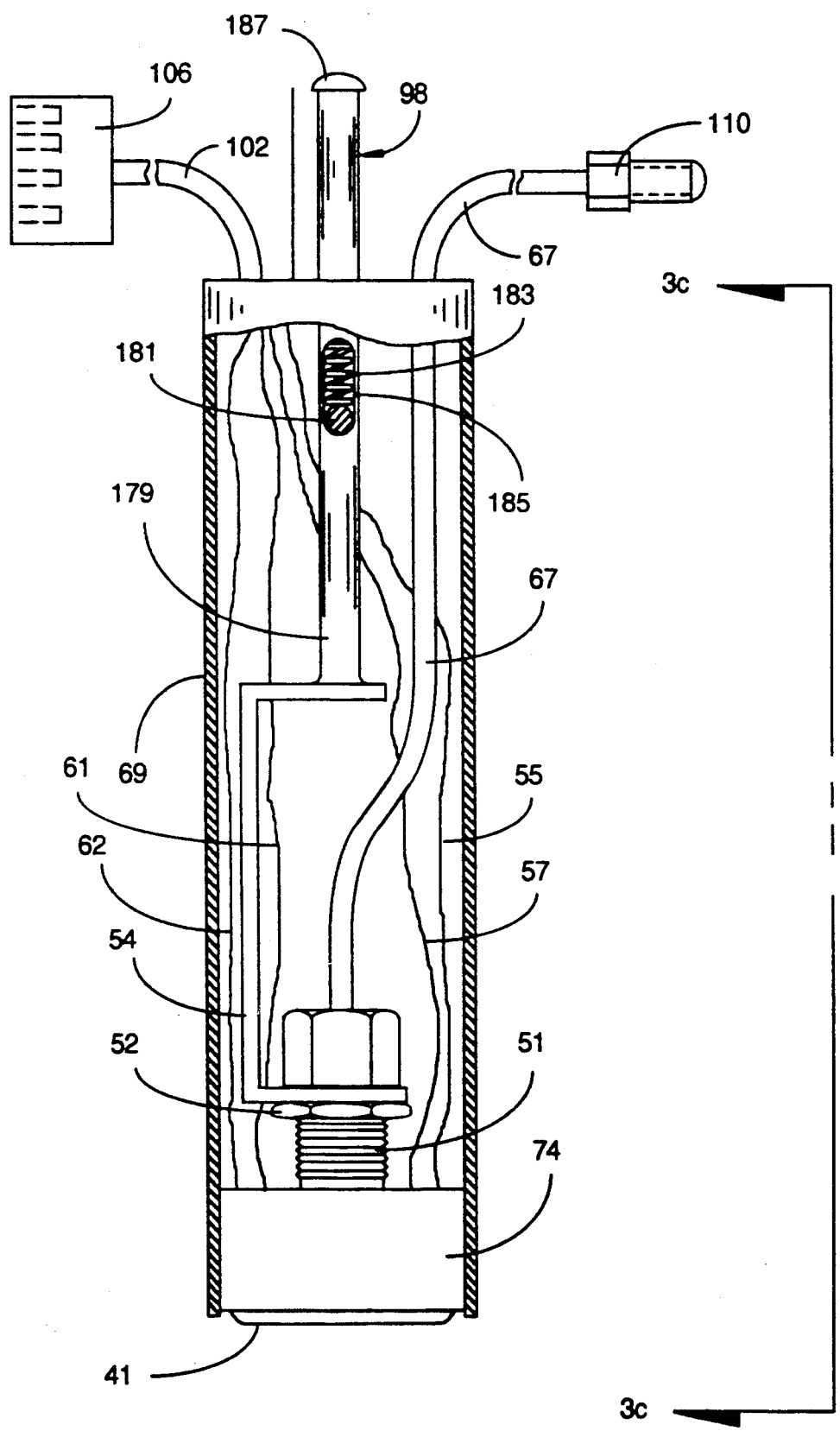
FIG. 3b is an elevation view of a single head, partly in section, showing an arrangement of elements for moving internal elements relative to the outer enclosure.

FIG. 3b is an elevation view, partially in section, of a single head to show additional detail of pusher assembly 98 not shown in FIG. 3a. The view of FIG. 3b is at 90 degrees to the view of FIG. 3a. Pusher assembly 98 comprises bracket 54 and a shaft 179 welded to the bracket. Shaft 179 is hollow and has a slot 185 through which a cross-pin passes. Although not shown in FIG. 3b, the cross-pin fixedly engages outer enclosure 69. A compression spring 183 is placed in the hollow shaft and held in by cap 187, which in the preferred embodiment is a button-head screw. The pusher assembly is fastened, as described above, to body 51 with the aid of lock-nut 52, so the body and elements attached to the body, will move with the pusher assembly.

Figure 3C:
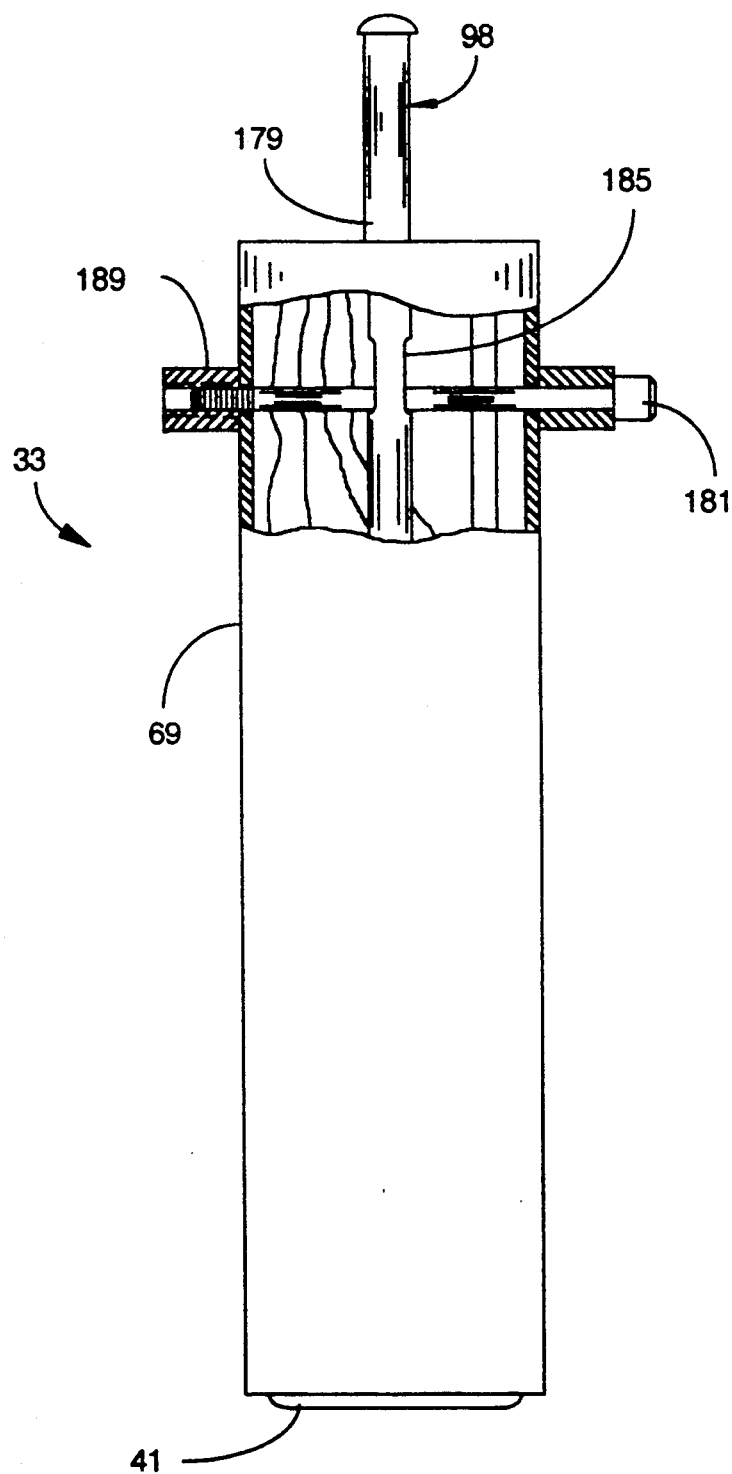
FIG. 3c is a view of a portion of the head of FIG. 3c, showing how a cross pin is anchored in a collar that is part of the head in a preferred embodiment.

FIG. 3c is a view of the head of FIG. 3b from the vantage of line 3c—3c of FIG. 3b, showing further detail of the pusher assembly and mounting. Cross pin 181 is, in the preferred embodiment, a socket-headed screw that passes through a portion of a collar 189 on one side of enclosure 69, through slot 185 of shaft 179, and threads into collar 189 on the opposite side of enclosure 69. Collar 189 is fixedly attached to enclosure 69. In the preferred embodiment, the attachment is by silver soldering.

Figure 3D:
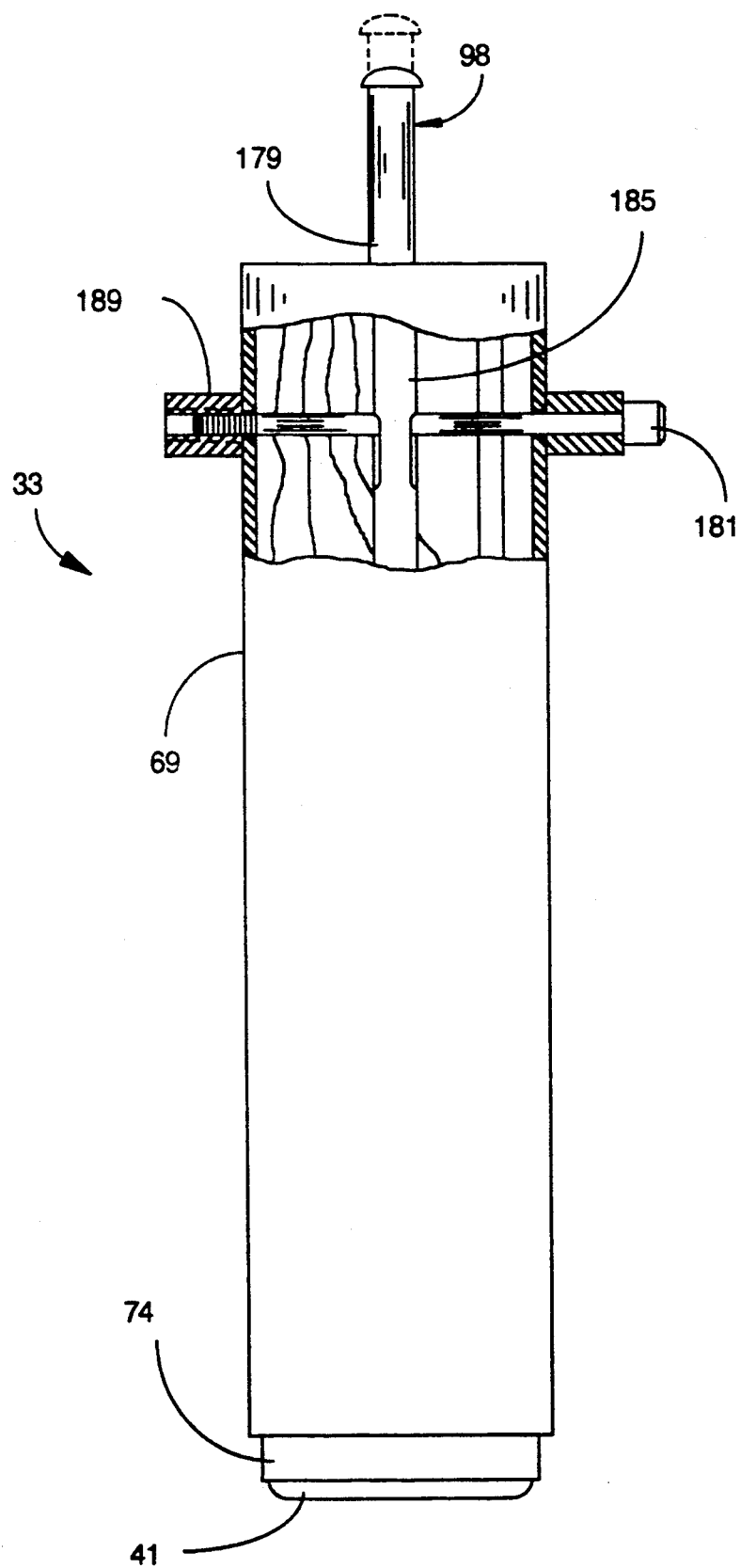
FIG. 3d lis similar to FIG. 3c, except the internal assembly is shown advanced from the external case to provide access for service.

Referring again to FIG. 3b, pressure applied to the capped end of shaft 179 of the pusher assembly while the head is held firm, will cause the lower portion of the head to extend from enclosure 69 by virtue of downward movement relative to the enclosure equal in distance to the length of slot 185. FIG. 3d shows the lower portion of the head extended. The purpose of the extension is to provide access to the lower portions of the head for service. For example, seal ring 41 may be easily removed and replaced without the need to pry the seal ring out with a tool. The pusher assembly described relative to one upper head 33 at a hydrolysis station is typical of the hydrolysis lower heads and the heads at a derivatizer station to be described as well.

FIG. 4a is an elevation view of three upper heads at a hydrolysis station, with elements to position and move the heads relative to the turret body of the station and the turrret of the instrument. Body 37, not shown in FIG. 4a. is typically cast metal in the preferred embodiment, machined to accept other elements of the station. Three guide bushings 191 fit into bores in the body, and three upper heads 33 are shown engaged and guided by the bushings. Lower heads 35 are engaged and guided in a similar manner, but illustration of the upper head arrangements and elements should be sufficient for understanding.

Each of the heads has a collar 189 as described above, and the heads pass through a carrier block 190 as well as being engaged in individual guide bushings 191, such that the collars 189 contact the carrier block. Each head is urged against the carrier block by a compression spring 71 that contacts collar 189 opposite the side that contacts the carrier block. The other end of each compression spring contacts a sheet metal cover 193 in the preferred embodiment that is fastened in turn to the cast body 37. Carrier block 190 has cam followers 99 and 197 pivotally attached on opposite sides. FIG. 4b is a view of the mechanism of FIG. 4a from the section line 4b—4b, and shows both cam followers. Cam rails 103 and 195 are fastened together and driven by a single electric motor to advance and retract the heads to contact sample slides in the station.

The lower heads at the hydrolysis station are similarly arranged with elements as described above, and are driven by the same electric motor to open and close the heads at the station to form and open reaction chambers.

DERIVATIZER STATION

After leaving the hydrolysis station, a sample slide on the indexing turret arrives at derivatizer station 109 after several indexes. The purpose of the derivatizer station is to tag the amino acids that are derived from the original polypeptide and to remove the amino acids from the sample supports and transfer them in the preferred embodiment for chromatographic analysis.

Figure 1D:
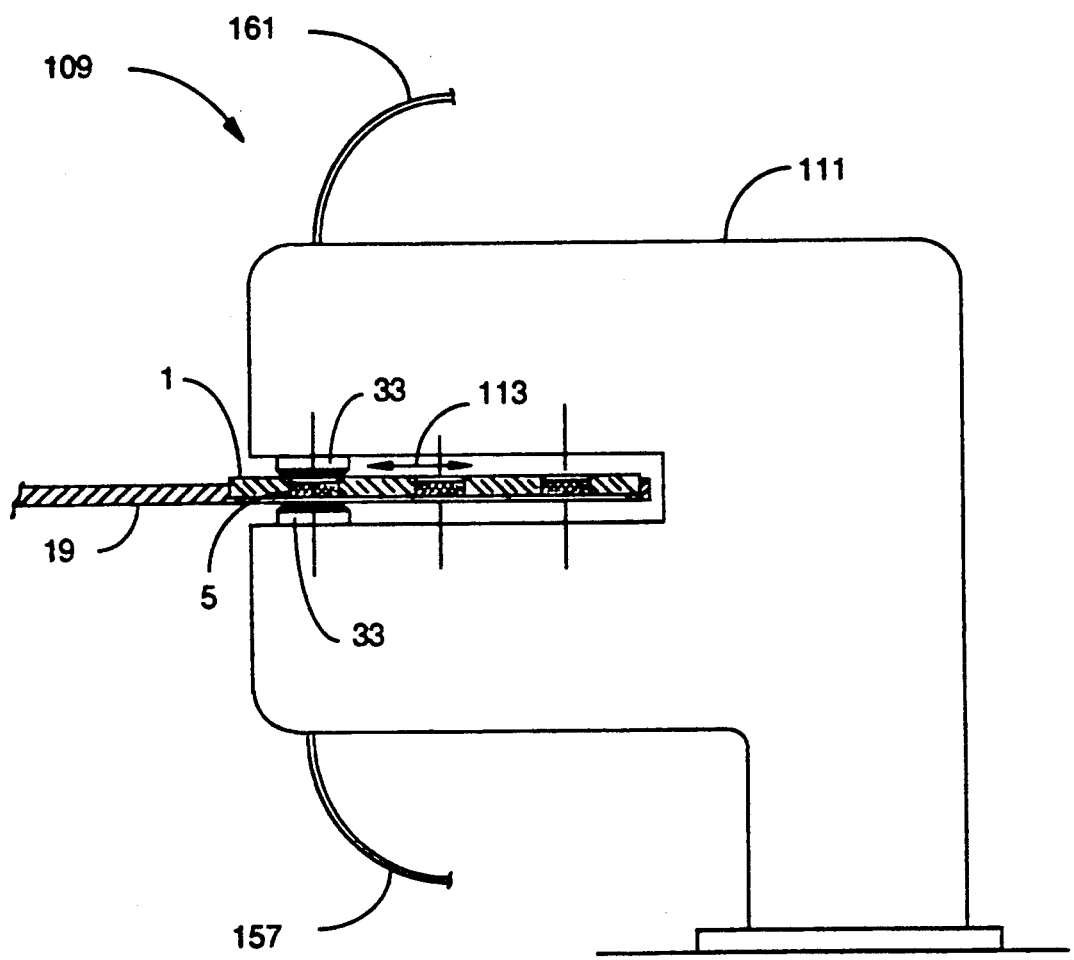

The derivatizer station is similar to the hydrolysis station in that there is an upper and a lower head that advance to form a reaction chamber with the sample slide, enclosing the sample support. The derivatizer station, however, has one pair of heads where the hydrolysis station has three pairs. FIG. 1d is an elevation view of the derivatizer station from the vantage of line 1d—1d of FIG. 1a, and in the direction of the arrows.

In FIG. 1d, heads 33 form an upper and lower set, and are substantially the same as heads 33 at the hydrolysis station. The inserted screw stud used in conjunction with head 35 at the hydrolysis station to lengthen the flow path for incoming substances is not required. The process performed at the derivatizer is completed for a single sample in a shorter time than the hydrolysis process typically requires at the hydrolysis station. Still, the process at the derivatizer has to be performed for each of the three sample supports in each sample slide in the preferred embodiment. To accomplish this purpose the cam rail and spring mechanisms for advancing the heads are essentially the same as used at the hydrolysis station, but additional mechanism and a second electric motor are provided so that the single set of heads can be moved back and forth in the direction of arrow 113 within body 111 while the heads are retracted. Body 111 is a casting in the preferred embodiment, similar to cast body 37 of the hydrolysis station. Power and control lines and fluid tubes connected to each of the derivatizer heads are a part of representative lines 157 and 161 shown leading away from the derivatizer station. The use of a single set of heads at the derivatizer station and three at the hydrolysis station in the preferred embodiment ensures that the derivatization is the controlling process from a timing viewpoint.

CONTROL AND OPERATOR INTERFACE

Control of the Hydrolysis/Derivatizer instrument in the preferred embodiment is through a Z-80 based microprocessor controller that is located within the instrument case. In other embodiments other microprocessors may be used, and the instrument may also be controlled by one or another of the well-known desk-top computers, such as the Apple Macintosh, a version of the IBM PC or PS/2, a model of an HP computer, or other of the general type.

In the preferred embodiment, and in alternative embodiments using other computer equipment, memory is allocated for storage of operating sequences and variables, and provision is made for displaying menus on a screen or other display for interface with an operator. There may also be embodiments of the invention in which stored sequences are not used for automatic control, and control is by operator initiation of separate functions through an interface.

Figure 5:
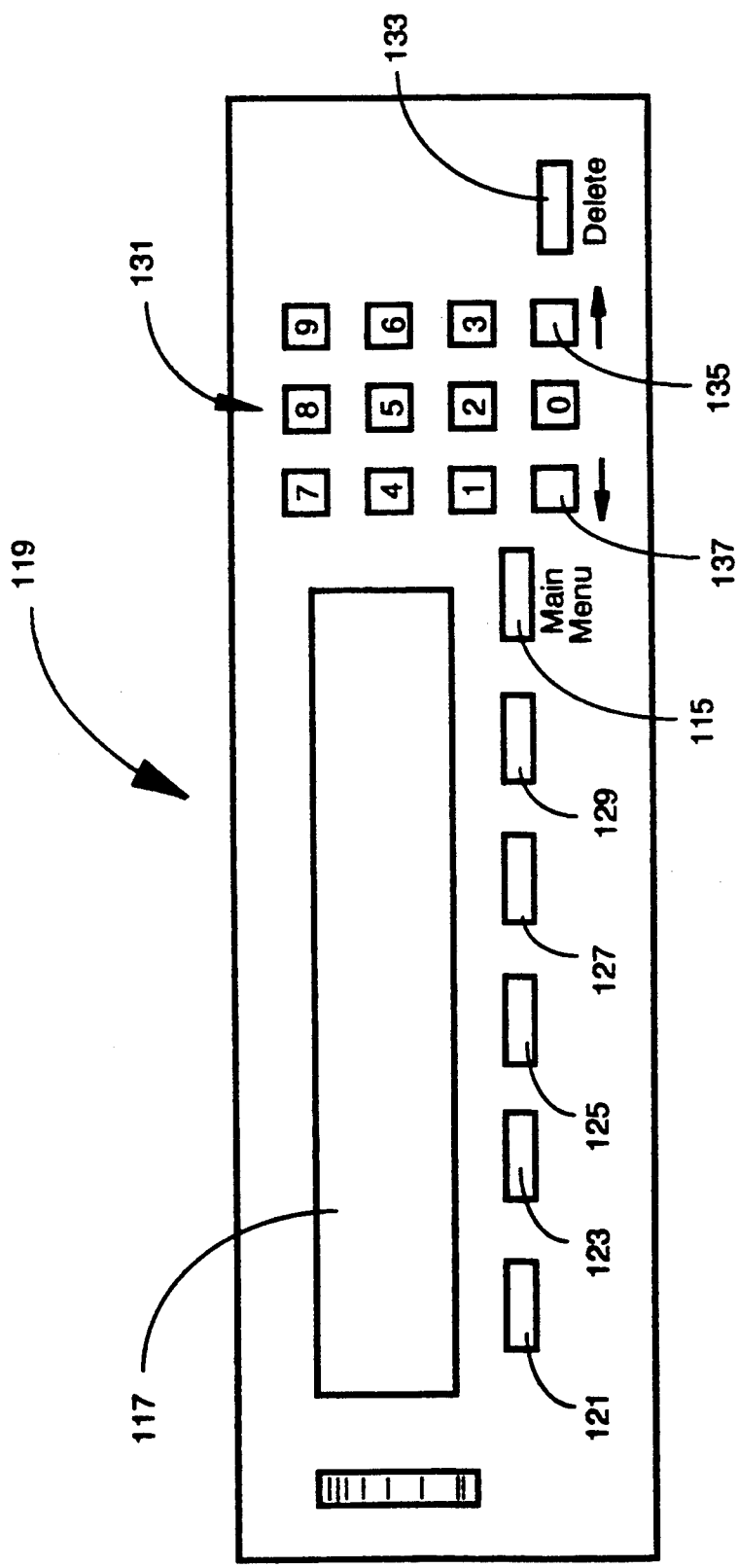
FIG. 5 shows an operator interface according to a preferred embodiment.

FIG. 5 shows an operator interface panel 119 located on the front of the instrument in the preferred embodiment. Key 115 is the Main Menu key, and provides a series of main menus on a two-line LCD display 117. The menu set-up is such that the LCD display provides labels above each of five soft-keys 121, 123, 125, 127, and 129, which may then be used to perform whatever function the label indicates. From Main Menu 115 the choices are second-level menus for such things as set-up of the hydrolysis procedures, set-up of the derivatizer procedure, and overall set-up of the instrument. Procedures may be set up in advance and stored, and then selected by number, and stored sequences and variables may be altered.

In the set-up and alteration procedures, a ten-key pad 131 is used to enter numerical amounts. The delete key 133 is used to delete numerical entries before storing. Arrow keys 135 and 137 are for moving a cursor position on the LCD display. There is a menu as well for manual control in which the soft keys may be used to perform functions one-at-a-time by an operator. Once set-up is performed or numbered procedures are chosen, operation commences by a start signal entered by depressing a soft-key at a system prompt. The system automatically cycles to a "home" position with the head retracted at the two stations and valves closed in the fluid feed subsystem, so a sample may be loaded. As new inputs are required from an operator prompts appear on the LCD display.

A TYPICAL PROCEDURE

In a typical procedure, a purified protein sample is applied to a sample support on a slide through the door on the front of the instrument. When the slide carrying the sample arrives at hydrolysis station 31 (FIG. 1a) the heads advance to clamp on the three sample support positions in the slide, creating three flow-through reaction chambers. Each of the upper and lower heads is connected by teflon fluid lines in the preferred embodiment to solenoid operated valve blocks. The upper heads are connected to valve block 139 by lines 140 and the lower heads to valve block 141 by lines 142. Lines 143 and 145 represent lines from valve blocks 139 and 141 to selected reservoir bottles 147 and 149. Line 151 represents fluid line connections to argon high pressure (4 psi) and low pressure (1 psi) supplies and to a waste container through appropriate manifolding.

Power to the motive devices and heaters in the heads and control sensing and control are supplied from a power and control module 153, comprising various appropriate power supplies and the Z-80 based control system. Representative lines are shown connecting the power and control module to various other elements as required.

After the reaction chambers are formed, an argon purge of all three chambers simulaneously is accomplished in preparation for hydrolysis reaction to be performed. After argon purge, HCl solution is delivered to the bottom of each reaction chamber, entering and filling the long spiral feed passage in each lower head. (see FIG. 3 and description of the lower head). All values close so that the reaction chamber for each sample support is a separate closed system, and the heaters are activated. The chambers are heated to a target temperature, typically 165° C., and each chamber is filled with HCl vapor. The temperature and pressure are held at the preprogrammed value for a preprogrammed time, which may vary from a few minutes to serveral hours, during which hydrolysis of the protein sample is accomplished.

The use of vapor drastically reduces the potential of contamination of the sample from the acid source, because minerals and other possible contaminants do not vaporize from the liquid acid solution. The acid concentration is typically 6 Normal (6N). The unique frit design described above presents a maximum surface area relative to sample volume to speed the reaction.

At the end of the preprogrammed hydrolysis time, the temperature is lowered to decrease the pressure in the chambers, which typically climbs as high as 60 psi. A stream of argon through the flow-through reaction chambers blows the acid out through the bottom to waste, and the samples are dried with a stream of argon. After a preprogrammed drying time, the heads are retracted, opening the reaction chambers, and the hydrolized samples are moved away by rotating the turret.

At the derivatizer station, the upper and lower head are each connected by fluid tubing to solenoid valve blocks, the upper to value block 155 by line 157, and the lower valve block 159 by line 161. Valve block 155 is connected through valving and representative line 162 to five reservoir bottles, 163, 165, 167, 169, and 171. Each of the reservoirs may be pressurized and valves activated to deliver fluids to the upper head. With the head clamped and forming a reaction chamber at one of the three sample positions, a drop of buffer solution, typically sodium acetate solution, is delivered into the feed line to the upper head by a short delivery, of the order of one second. Valves are switched and the solution is blown gently through the line until it reaches the sample support, where it wets the support and the sample.

After a preprogrammed time, the dissolved sample is blown out of the chamber, through valve block 159 via line 173 to a transfer flask 175. The procedure is typically repeated, doing a second operation with buffer on the same sample support, then the two portions of dissolved sample in the transfer flask are moved by argon pressure via line 78, and via a valve block 199 to a connected chromatographic instrument via line 177. The upper head at the derivatizer station is connected through valve block 159 via representative lines 201 to the high pressure, low pressure and waste manifolds.

It will be obvious to one skilled in the art that not all of the fluid lines or power or control lines are indicated on the block diagram of FIG. 1a, nor are the many complicated connections and solenoid valves, among many other elements. The block diagram was meant to be representative, and the power and control connections, and the fluid and pneumatic system details to accomplished the various tasks are generally known.

After the derivatives are dissolved and transferred at each sample support a cleaning procedure is activated with a solvent flushed through the support and the lines, followed typically by purging with a dry inert gas, such as argon. In the preferred embodiment the solvent is typically methanol. The heads then open and the set moves to the next sample support in the slide, where the procedure is repeated. After derivatization and cleaning of the sample supports the heads retract and the turret indexes to move the sample slide away from the derivatizer station, and to bring a new slide to the station.

The multiple slide positions, the variety of valving arrangements that may be made, and the ability tp operate manually as well as to program procedures provides a flexible system for hyrolysis and derivatization of many protein samples with a high degree of repeatability and automation, as well as a minimum risk of contamination.

TYPICAL RESULTS

FIG. 6 is a chart of typical results using the Hydrolyzer/derivatizer of the preferred embodiment with several purified protein samples. The leftmost column identifies the several constituent amino acids (AA), the protein names are listed across the upper band (Hemoglobin, Pepsin, etc.), and the bottom three rows list the total number of residues, the Molecular Weight, and the amount hydrolyzed in micro-grams for each sample. Each column below a protein name lists the residue numbers experimentally determined for each amino acid for each protein, with the expected result in parentheses.

It will be apparent to one skilled in the art that there are a large variety of changes that may be made without departing substantially from the spirit and scope of the invention. For example, the number of slide positions on a turret may be varied. Also the arrangement of values and controls may be altered in many ways. Dimensions may be changed and materials substituted. An instrument may be provided within the scope of the invention to perform hydrolysis only, without the derivatization station, and an instrument may likewise have, a derivatization station without an hydrolysis station. The number of stations may vary, and the number of head sets at a signal station may vary as well. The use of three sample supports in a slide is for convenience, and there may be more or fewer. Such changes are to be seen as changes in detail, and will not depart from the spirit and scope of the invention.

What is claimed is:

1. An apparauts for performing hydrolysis of proteins comprising:
 a substantially flat sample slide with a hole therethrough;
 porous sample support means for supporting a protein sample during processing, said sample support means contained within said hole in said sample slide;

transport means for transporting said sample slide from a start position, to processing stations, and to a finish position after processing performed;

a hydrolysis station for performing hydrolysis of a protein sample delivered by said transport means, said hydrolysis having movable heads with seal means, such that said heads enclose said sample support means during processing, said seal means contacting surfaces of said sample slide forming a sealed reaction chamber for hydrolysis to be performed on said protein sample; and substance delivery means for delivering substances to said reaction chamber through fluid lines connected to said heads, and for removing substances from said reaction chamber.

2. Apparatus for performing hydrolysis of proteins as in claim 1 wherein said porous sample support means is a structure of rods, each rod adherent to adjacent rods, forming a porous volume such that fluids may pass through from one side of said sample slide to the other side while said porous sample support means supports said protein sample.

3. Apparatus for performing hydrolysis of proteins as in claim 2 wherein said sample slide and said sample support are formed from glass.

4. Apparatus for performing hydrolysis of proteins as in claim 1 wherein said transport means comprises a rotating turret, said turret having one or more openings configured to support one of said sample slides, such that opposite sides of said sample slide are exposed to said seal means of said heads to form a closed reaction chamber with said sample slide.

5. An apparatus for performing hydrolysis of proteins as in claim 1 wherein one of said heads further comprising a heater for heating substances within said reaction chamber.

6. An apparatus for performing hydrolysis of proteins as in claim 1 wherein one of said heads further comprises a spiral passage for substances introduced to said reaction chamber said spiral passage formed by a threaded stud inserted into a clylindrical passage through said head such that a fluid entering through said passage passes the full length of said spiral passage.

7. An apparatus for performing hydrolysis of proteins as in claim 1 wherein said substance delivery means comprises solenoid operated valves connected to said fluid lines connected to said heads, fluid reservoirs connected to said valves for storing substances to be introduced to said reaction chamber, a gas mainfold connected to said valves for urging substances through said fluid lines and for purging said reaction chamber, and waste disposal means for disposing of waste materials from said reaction chamber.

8. Apparatus for performing hydrolysis of proteins as in claim 1 additionally comprising computerized control means for controlling sequences of operations under programmed control.

9. Apparatus for performing hydrolysis of proteins as in claim 1 additionally comprising a derivatizer station for automatically removing amino acid derivatives from said sample support means after hydrolysis and delivering said derivatives for chromatographic analysis, said derivatizer station having moveable heads with seal means such that said heads enclose said sample support means during processing at said derivatizer station, said seal means contacting surfaces of said sample slide forming a sealed chamber for derivatization to be performed.

* * * * *